United States Patent [19]
Takaishi et al.

[11] 3,976,711
[45] Aug. 24, 1976

[54] PROCESS FOR THE PREPARATION OF TRICYCLO[5.3.1.0$^{3,8}$]UNDECANE

[75] Inventors: Naotake Takaishi; Yoshiaki Inamoto, both of Wakayama; Kiyoshi Tsuchihashi, Kainan, all of Japan

[73] Assignee: Kao Soap Co., Ltd., Tokyo, Japan

[22] Filed: June 3, 1975

[21] Appl. No.: 583,422

[30] Foreign Application Priority Data
June 4, 1974 Japan................................ 49-63237

[52] U.S. Cl........................ 260/666 PY; 260/666 M
[51] Int. Cl.$^2$.......................................... C07C 13/54
[58] Field of Search.................. 260/666 PY, 666 M

[56] References Cited
OTHER PUBLICATIONS
Naotake Takaishi et al., J. Org. Chem. 40 No. 3, pp. 276–281, 1975.
Majerski et al., Tetrahedrou Letters, 4915, 1973.
Krantz et al., Chem. Commun. 1971, 1287.
Krantz et al., J. Amer. Chem. Soc. 95, 5662, 1973.
Schleyer et al., Chem. Letters, 1189, 1973.
N. S. Vorobeva, O. A. Arefev, V. I. Epshev, and A. A. Petrov, [Neftekhimiya, 11, 163, 1971] Chem. Ab. 75: 19562e.

*Primary Examiner*—Veronica O'Keefe
*Attorney, Agent, or Firm*—Woodhams, Blanchard and Flynn

[57] ABSTRACT

A process for the preparation of tricyclo [5.3.1.0$^{3,8}$]undecane in which homoadamantane is isomerized in the presence of an acid catalyst.

5 Claims, No Drawings

PROCESS FOR THE PREPARATION OF TRICYCLO[5.3.1.0³·⁸]UNDECANE

BACKGROUND OF THE INVENTION

1. FIELD OF THE INVENTION

This invention relates to isomerization of homoadamantane. More particularly, this invention relates to a process for preparing tricyclo[5.3.1.0³·⁸]undecane (II) (hereinafter referred to as "4-homoisotwistane") by isomerizing homoadamantane (I) as shown by the following reaction scheme:

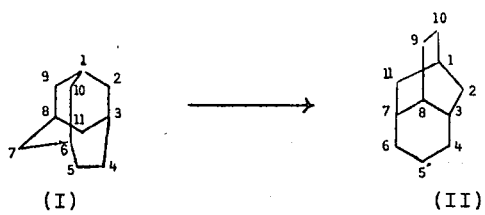

As is seen from formula (II), 4-homoisotwistane (II) is a tricyclic saturated aliphatic hydrocarbon having a cagelike molecular structure. It can be transformed to 1-methyladamantane, a known useful compound as described in U.S. Ser. Nos. 485,068 and 485,069, both filed July 2, 1974 now U.S. Pat. No. 3,894,100 and 3,894,101 respectively. In view of its molecular structure, 4-homoisotwistane will be useful as an antiviral agent, a modifier moiety for various pharmaceutical compounds, an additive for lubricating oils, a high-pressure lubricant, a rust-preventive agent, an oiling agent for fibers and the like, in the same manner as known adamantane compounds. See the section entitled "Adamantane" in the Supplement Volume of Kirk-Othmer's "Encyclopedia of Chemical Technology".

2. DESCRIPTION OF THE PRIOR ART

Several processes for the synthesis of 4-homoisotwistane (II) are known in the art. For example, the synthesis of this compound is disclosed by Krantz et al, *Chem. Commun.*, 1287 (1971) and *J. Amer. Chem. Soc.*, 95, 5662 (1973), Majerski et al, *Tetrahedron Lett.*, 4915 (1973), and Schleyer et al, *Chemistry Lett.*, 1189 (1973).

We previously found that 4-homoisotwistane (II) can be synthesized by isomerizing, in the presence of an acid catalyst, 5,6-exo-tetramethyleneorbornane (III) of the following formula:

and 5,6-trimethylenebicyclo[2.2.2]octane (IV) of the following formula:

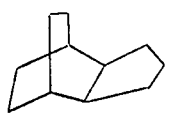

(see Chemistry Lett., 1185, (1973) and Japanese Patent Applications No. 77621 (U.S. Ser. No. 485 068 now U.S. Pat. No. 3,894,100) and No. 77622/73 (U.S. Ser. No. 485 067)).

SUMMARY OF THE INVENTION

As a result of our further research, we discovered that homoadamantane can be isomerized to a mixture containing 4-homoisotwistane (II) under specific reaction conditions. Based on this finding, we have now completed this invention.

It is known that when homoadamantane (I) is isomerized in the presence of acid catalyst, a mixture of 1- and 2-methyladamantanes can be obtained (K. R. Blanchard, Ph, D. Thesis, Princeton Univ. (1966)), but it is not disclosed therein whether or not 4-homoisotwistane is formed as an intermediate during this isomerization reaction. Further, it is not even suggested whether or not there could exist any reaction conditions that convert homoadamantane (I) to a mixture containing 4-homoisotwistane (II).

Homoadamant-4-ene (V) of the following formula:

and homoadamantan-4-ol (VI) of the following formula:

are the only compounds possessing the homoadamantane skeleton which can be isomerized to 4-homoisotwistane (Majerski et al, Tetrahedron Lett., 4915 (1973)). In this reference, there is disclosed a mechanism in which the homoadamant-4-yl cation (VII) of the following formula:

formed by addition of a proton to the compound (V) or by removal of a hydroxyl anion from the compound (VI), is isomerized. In view of the relative stabilities of various bridgehead cations from polycycloalkanes (R. C. Bingham and P. V. R. Schleyer, J. Amer. Chem. Soc., 93, 3189 (1971)), ionization of the homoadamantane molecule in the presence of an acid should give rise to a homoadamant-3-yl cation (VIII) of the following formula:

The course of an isomerization reaction involving a bridgehead tertiary carbon atom cation as in (VIII) cannot be predicted, based on the course of an isomerization reaction involving a bridgehead secondary carbon atom cation as in (VII). Accordingly, the reaction process of this invention cannot be expected from the results reported by Majerski et al.

As pointed out hereinabove, when homoadamantane is isomerized in the presence of an acid catalyst, there is obtained a mixture of 1- and 2-methyladmantanes as a final product. We found that if suitable reaction conditions are employed, a mixture containing a number of reaction intermediates including 4-homoisotwistane (II) can be isolated. These intermediates are formed at various stages of the complication reaction course starting from (I), which comprises a complex combination of consecutive and competitive reactions. When the reaction is stopped partway to completion, there is obtained a mixture containing such intermediates at a ratio determined by the reaction conditions and the reaction time. We discovered that if the reaction conditions such as the types and amounts of the catalyst and solvent, as well as the reaction temperature and time, are appropriately chosen in the above reaction, there can be obtained a reaction product mixture in which the proportion of 4-homoisotwistane (II) in the reaction mixture is a maximum, usually at least about 15 weight percent.

As is apparent from the foregoing, 4-homoisotwistane (II) can be prepared from the starting homoadamantane (I). However, since homoadamantane (I) is finally converted to 1- and 2-methyladamantanes as described hereinabove, in order to recover in high yield 4-homoisotwistane (II) formed as an intermediate, it is necessary to perform the reaction under limited conditions. The term "reaction under limited conditions" means a reaction in which isomerization is stopped at an appropriate time, a reaction in which the amount of the catalyst is reduced or in which a catalyst having a relatively low activity is used, a reaction in which isomerization is carried out in the presence of a solvent, a reaction in which isomerization is carried out at a relatively low temperature, and a reaction which is carried out using an appropriate combination of two or more of these reaction procedures. The isomerization reaction under limited conditions is carried out so that the isomerization reaction is stopped at a stage at which the content of [5.3.1.0$^{3,8}$]undecane in the reaction mixture is at least about 15 weight percent, and is preferably at the highest level that can be attained under the reaction conditions which is usually at least 20 weight percent.

In contrast, when the reaction is carried out under such drastic conditions as the use of strong Lewis acid catalysts such as aluminum halides and antimony pentahalides in as large an amount as 50 mole percent or more based on the starting substance (I) in the absence of solvents, at elevated temperatures exceeding about 50°C., the starting material (I) is promptly converted to final methyladamantanes, while various intermediates exemplified by 4-homotwistane (II), which is the intended product of this invention, are hardly detected.

In order to establish the limited reaction conditions employed in the process of this invention, there can be used as catalyst Brønsted acids such as sulfuric acid, fluorosulfonic acid, chlorosulfonic acid, alkanesulfonic acids, e.g., methanesulfonic acid, trifluoromethanesulfonic acid and ethanesulfonic acid, and arenesulfonic acids, e.g., benzenesulfonic acid, and p-toluenesulfonic acid. The amount of such Brønsted acid catalysts can be from 0.01 to 20 moles, preferably from 0.1 to 10 moles, per one mole of starting substance (I). Further it is possible to use as catalyst a Lewis acid such as aluminum halides, boron trifluoride and antimony pentahalides in a limited amount of from 0.001 to 0.5 moles, per one mole of the starting substance (I). In order to complete the reaction in a short time, Brønsted acids can be used in an equivalent amount or excess, but Lewis acids, in order to avoid extensive reaction of the once-formed intermediates, should be used in amounts not exceeding 50 mole percent. These catalysts can be used in the form of a mixture of two or more of them. For instance, if a combination of sulfuric acid and boron trifluoride is used, a synergistic effect is observed.

In the process of this invention, favorable results are often obtained if a solvent is used, in addition to the abovementioned appropriate selection of the kind and amount of the catalyst. One of the reasons therefor is that the starting substance (I) is solid at room temperature. The type of the solvent used is not critical. Any solvents which are inert to the catalyst, such as aromatic hydrocarbons, aliphatic hydrocarbons, halogenated hydrocarbons and ethers, can be used. Further, these solvents can be used in combination with any of the foregoing catalysts (and mixtures thereof). Moreover, the amount used of the solvent is not critical. For example, the amount of the solvent can be from 0.1 to 500 times the weight of the starting material (I).

The isomerization reaction of the process of this invention proceeds at temperatures ranging from −30°C. to + 100°C., but it is preferred to carry out the reaction at −10°C to +50°C.

A preferred embodiment of this invention will now be described in detail by reference to the following illustrative Example.

EXAMPLE 1

A solution of 3.0 g (0.02 mole) of homoadamantane (I) in 50 ml of methylene chloride was stirred at 0°C. and 12.0 g (0.08 mole) of trifluoromethanesulfonic acid was added to the solution. Then, the mixture was heated to reflux for 1 hour.

The reaction mixture was allowed to cool and poured onto 50 ml of ice-water to separate into an organic and an aqueous layer. The aqueous layer was extracted with methylene chloride. The combined methylene chloride extract and organic layer were washed with a saturated aqueous solution of sodium hydrogen carbonate and water, and dried over anhydrous sodium sulfate. Evaporation of the methylene chloride gave a mixture of tricycloundecanes, which was then fractionated and purified on gas chromatography (SE-30; column temperature = 80°C.) to recover 0.6 g (yield = 20%) of tricyclo[5.3.1.0$^{3,8}$]-undecane (II).

Melting Point (sealed tube): 62°–63°C.

Elemental Analysis: Found: C, 87.8; H, 12.3 Calculated for $C_{11}H_{18}$: 87.92; H, 12.08 ir (cm$^{-1}$): 2925, 2890, 2870, 2850, 1480, 1465, 1450, 1440, 1340, 975, 940, 895, 845 ms (m/e) (relative intensity, %): 150 (M$^+$, 100), 122 (39), 121 (39), 109 (12), 108 (16), 107 (19), 93 (27), 81 (27), 80 (46), 79 (40), 67 (35), 55 (18), 41 (40)

$^1$H nmr (CDCl$_3$, δ): 1.0 – 2.0, complex multiplet $^{13}$C nmr (CDCl$_3$ solvent, 15.1 MHz, TMS at 0 ppm) (ppm): 15.2, 24.8, 26.3, 27.1, 30.9, 31.9, 32.3, 33.1

The embodiments of this invention in which an exclusive property or privilege is claimed are defined as follows:

1. A process for preparing tricyclo[5.3.1.0$^{3,8}$]undecane (II) which comprises isomerizing homoadamantane (I), at a temperature in the range of from −30° to +100°C., in the presence of an acid catalyst selected from the group consisting of (1) at least one Br∅nsted acid, and (2) at least one Lewis acid in an amount of 0.001 to 0.5 mole per mole of I; terminating the isomerization reaction when the content of II in the reaction mixture is at least about 15 weight percent; and recovering II from the reaction mixture.

2. The process according to claim 1 wherein the temperature of the isomerization reaction is in the range of −10° to 50°C.

3. The process according to claim 1 in which the acid catalyst is at least one Br∅nsted acid selected from the group consisting of sulfuric acid, fluorosulfonic acid, chlorosulfonic acid, methanesulfonic acid, trifuloromethanesulfonic acid, ethanesulfonic acid, benzenesulfonic acid and p-toluenesulfonic acid.

4. The process of claim 1 in which the acid catalyst is at least one Lewis acid selected from the group consisting of boron trifluoride, aluminum halides and antimony halides.

5. The process of claim 1 in which the isomerization reaction is carried out in the presence of an inert solvent.

* * * * *